(12) United States Patent
Costabile

(10) Patent No.: US 11,013,613 B2
(45) Date of Patent: May 25, 2021

(54) IMPLANTS AND GUIDES FOR INSERTING AN IMPLANT

(71) Applicant: Alphatec Spine, Inc., Carlsbad, CA (US)

(72) Inventor: Jonathan T. Costabile, San Diego, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days.

(21) Appl. No.: 16/209,937

(22) Filed: Dec. 4, 2018

(65) Prior Publication Data

US 2019/0374347 A1 Dec. 12, 2019

Related U.S. Application Data

(62) Division of application No. 15/273,847, filed on Sep. 23, 2016, now Pat. No. 10,143,567.

(60) Provisional application No. 62/222,552, filed on Sep. 23, 2015.

(51) Int. Cl.
| | |
|---|---|
| *A61F 2/30* | (2006.01) |
| *A61F 2/44* | (2006.01) |
| *A61F 2/46* | (2006.01) |
| *A61F 2/28* | (2006.01) |

(52) U.S. Cl.
CPC .......... *A61F 2/447* (2013.01); *A61F 2/30771* (2013.01); *A61F 2/4611* (2013.01); *A61F 2002/2835* (2013.01); *A61F 2002/30827* (2013.01); *A61F 2002/30828* (2013.01); *A61F 2002/30904* (2013.01); *A61F 2002/4622* (2013.01); *A61F 2002/4627* (2013.01); *A61F 2002/4687* (2013.01)

(58) Field of Classification Search
CPC .... A61F 2/30771; A61F 2/447; A61F 2/4611; A61F 2002/2835; A61F 2002/30827; A61F 2002/30828; A61F 2002/30904; A61F 2002/4622; A61F 2002/4627; A61F 2002/4687
USPC ....... 623/17.11–17.16; 606/246–279, 96, 90, 606/99, 100, 86 R, 86 A
See application file for complete search history.

(56) References Cited

U.S. PATENT DOCUMENTS

| | | | | |
|---|---|---|---|---|
| 3,486,505 | A * | 12/1969 | Morrison | A61B 17/025 606/90 |
| 7,575,576 | B2 * | 8/2009 | Zubok | A61F 2/4611 606/90 |
| 7,951,202 | B2 * | 5/2011 | Ralph | A61B 17/025 623/17.11 |
| 8,465,547 | B2 * | 6/2013 | Melkent | A61F 2/447 623/17.16 |
| 8,679,184 | B2 * | 3/2014 | Kube, II | A61F 2/4611 623/17.16 |
| 9,408,721 | B2 * | 8/2016 | Eastlack | A61F 2/4611 |

(Continued)

*Primary Examiner* — Pedro Philogene
(74) *Attorney, Agent, or Firm* — Robert Winn

(57) ABSTRACT

A system and a method for performing a spinal procedure configured to minimize the size of the surgical corridor so as to reduce recovery time is provided. The system and method include an implant and a guide. The guide is configured to be disposed within a surgical corridor formed by an instrument. The instrument is removed wherein the muscles may contract onto the guide so as to reduce the surgical corridor, wherein the implant is slid down the surgical corridor between a pair of guide members.

13 Claims, 13 Drawing Sheets

(56) References Cited

U.S. PATENT DOCUMENTS

RE46,410 E * 5/2017 Fraser .................. A61F 2/4611
2014/0343559 A1* 11/2014 Flickinger ............. A61F 2/4611
606/90

* cited by examiner

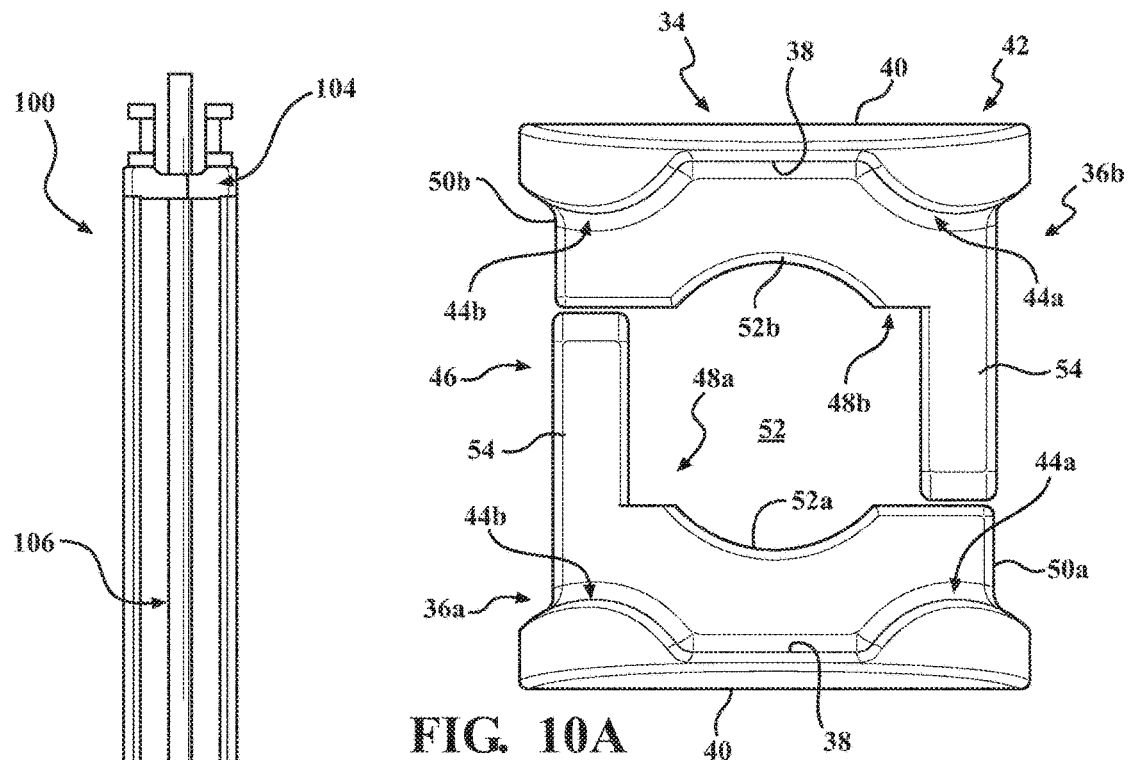
FIG. 10A
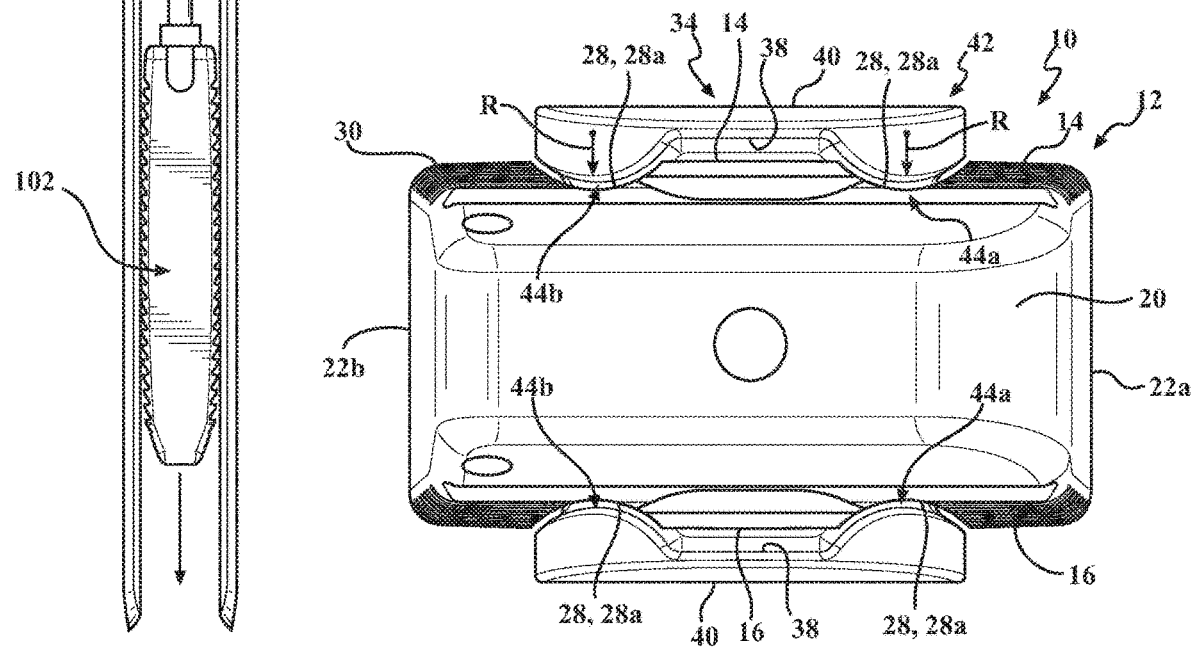
FIG. 9
FIG. 10B

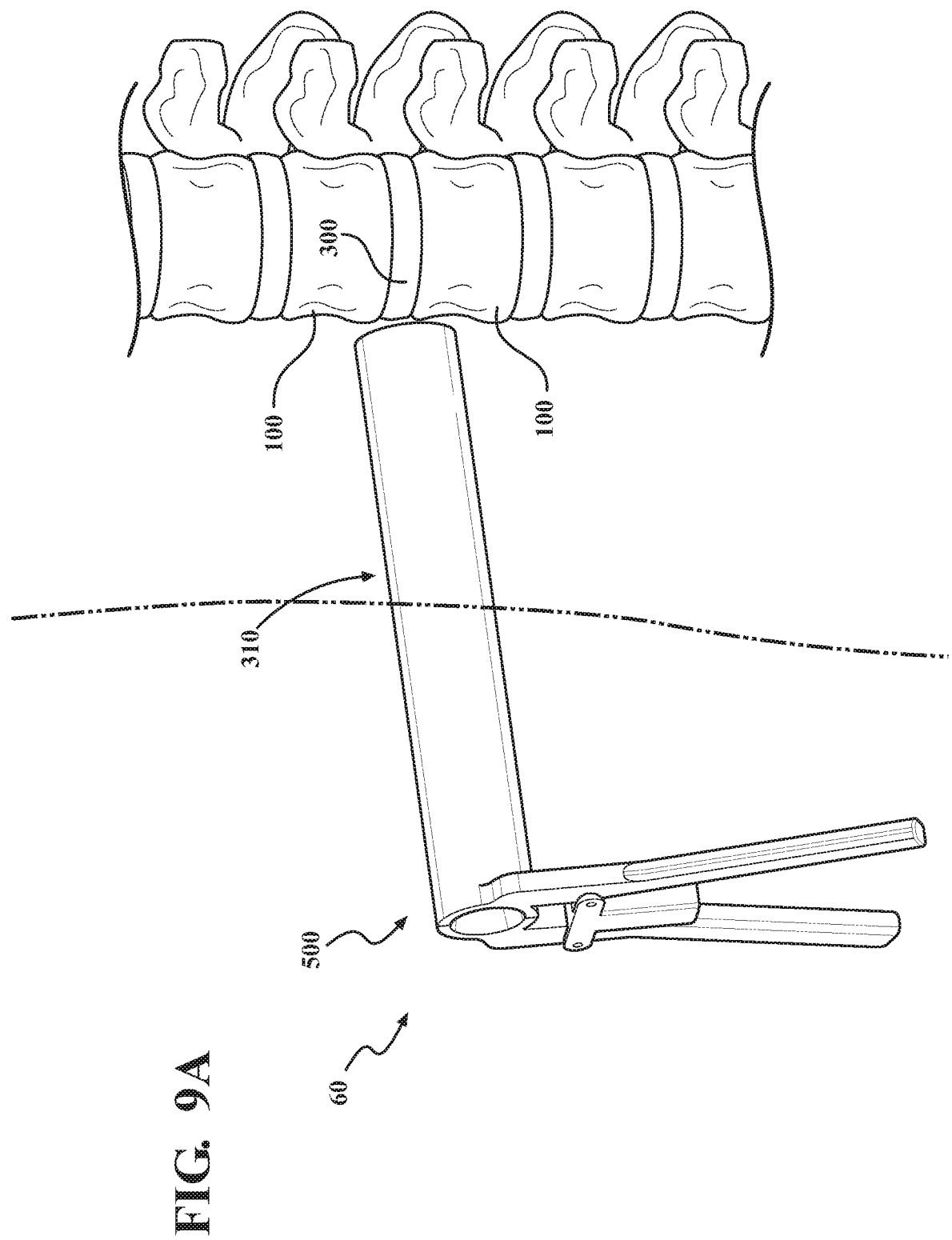

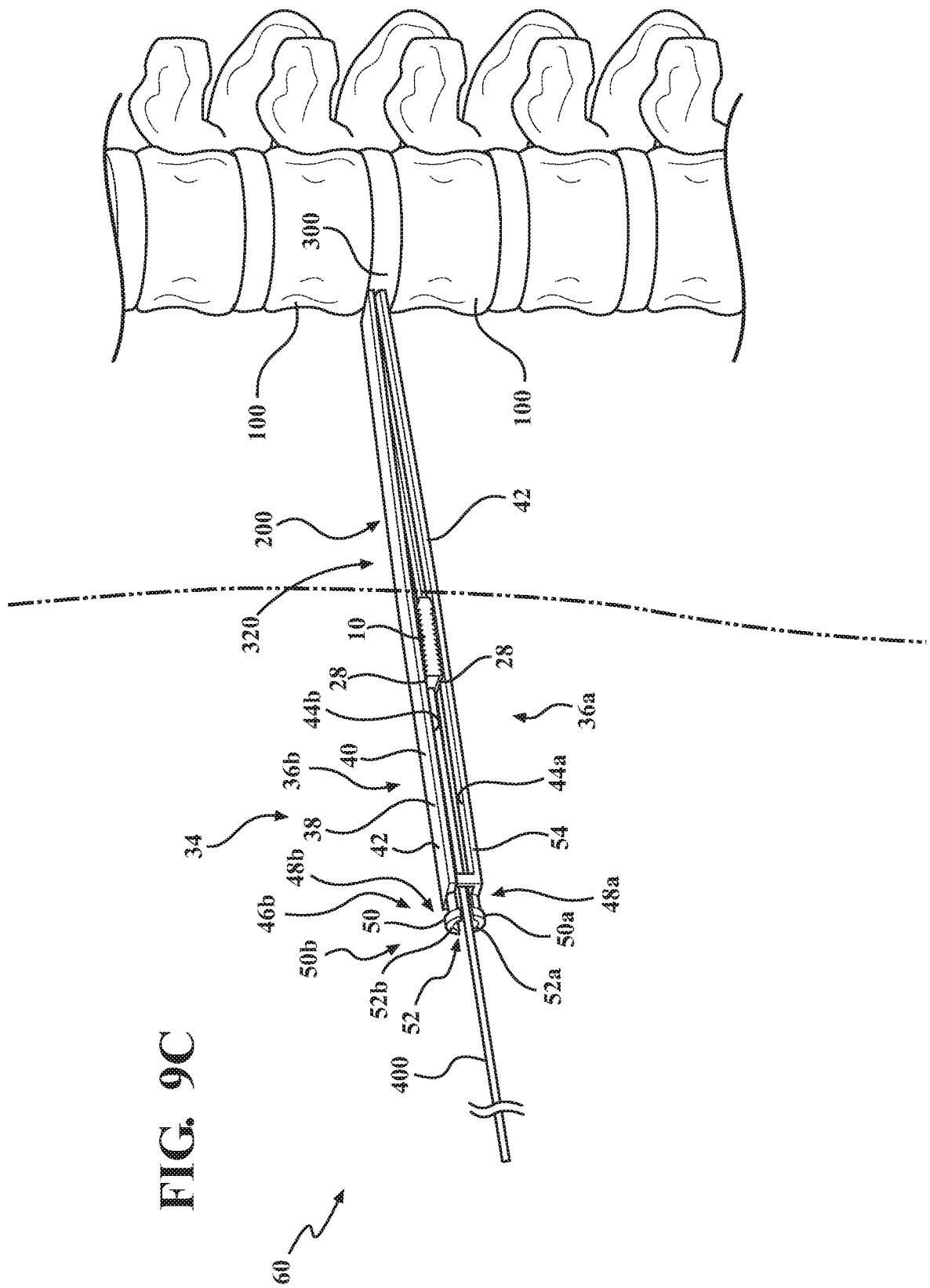

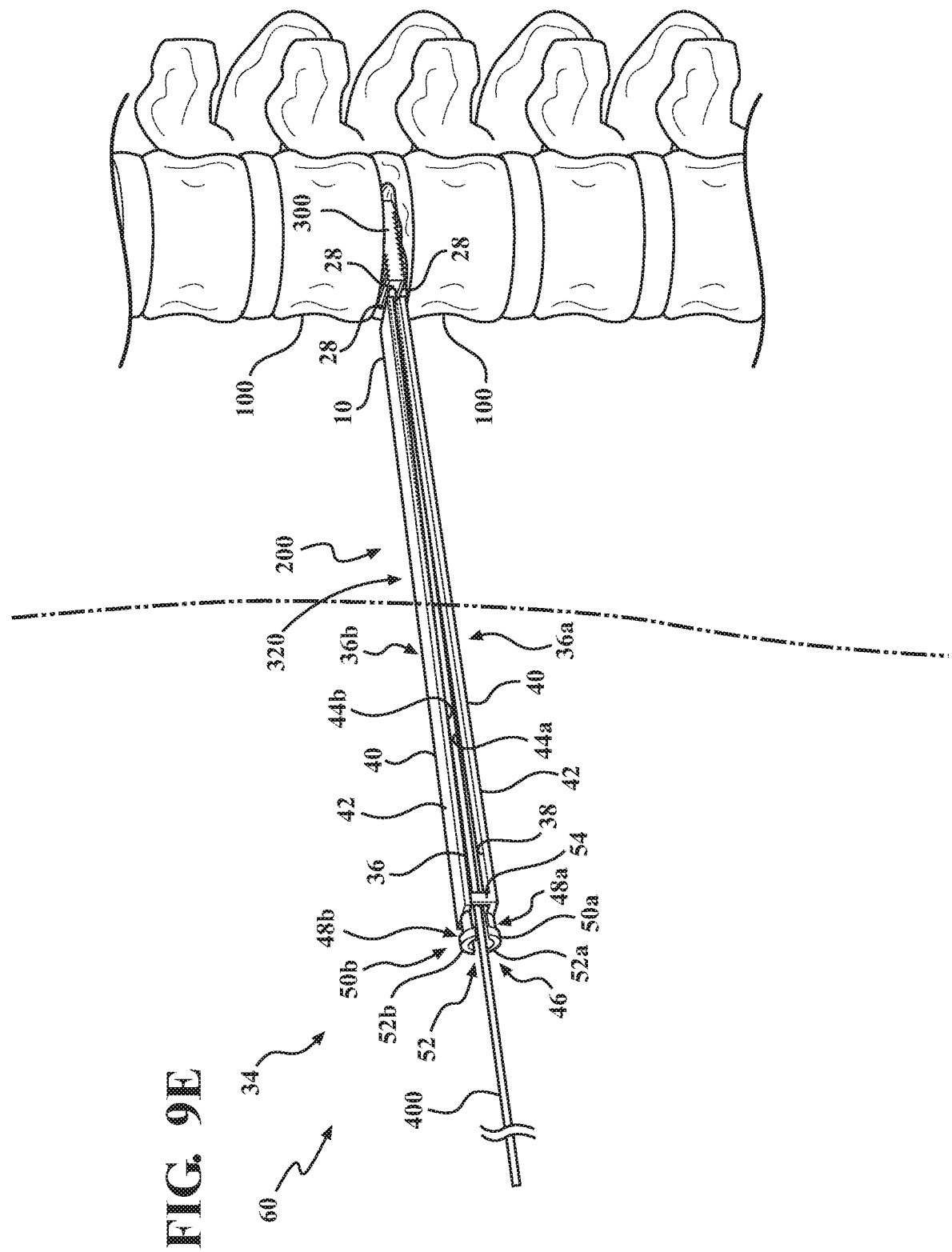

IMPLANTS AND GUIDES FOR INSERTING AN IMPLANT

CROSS-REFERENCE TO RELATED APPLICATIONS

This application is a divisional application of U.S. application Ser. No. 15/273,847, filed Sep. 23, 2016, which claims priority to U.S. Provisional Application No. 62/222,552, filed Sep. 23, 2015, the contents of both of which are incorporated herein by reference.

FIELD OF THE INVENTION

An implant, a guide for inserting the implant, and a system and method for inserting an implant in a surgical corridor so as to reduce recovery time for a patient are provided.

BACKGROUND

Minimally invasive spinal surgeries are known. Such procedures include an implant directed to be inserted between a pair of adjacent vertebrae. The insertion of the implant is done through a surgical corridor which is formed by an instrument such as a retractor with retractor blades. The surgical corridor is dimensioned to allow the implant to pass through so as to place the implant into a surgical site. Accordingly, the retractor blades hold the muscles apart for the duration of the implant process.

However, it is known that the extension of muscle at a surgical site for a prolonged period of time has a direct relationship to the recovery time for a patient. In particular, the longer the retractor holds the muscles apart the longer the recovery time. The muscles are held apart to form the surgical corridor for not only the period of time needed to insert the implant into the surgical site, but also the time to fill the space within the implant body with bone graft material. Accordingly, it remains desirable to have a guide configured to reduce the expansion time of the muscles so as to minimize recovery time.

Further, current retractors provide a surgical corridor for which the implant is passed through. The surgical corridor provides a predetermined amount of tolerance between the inner surface of the retractor blades and the outer surface of the implant. Thus, the surgeon passes the implant through the surgical corridor free handed. Accordingly, it remains desirable to have a guide configured to retain the implant along an axial path of the surgical corridor towards the surgical site.

SUMMARY

An implant having a body with a pair of grooves on superior and inferior surfaces of the implant is provided. The implant is adaptable for use with a guide. The guide includes a pair of guide members and a clasping mechanism. Each guide member includes an elongated member. The clasping mechanism is disposed on the proximal ends of the elongated members. The clasping mechanism is configured to hold the pair of elongated members together such that the proximal ends of the guide are spaced apart from each other a predetermined distance.

The elongated members further include a pair of ribs extending axially on opposite sides. The ribs are formed on respective inner surfaces of the guide members and are configured to engage corresponding grooves on the superior and inferior surfaces of the implant.

The clasping mechanism includes a pair of clasping members configured work together to maintain a spatial distance between proximal ends of the respective guide members. The clasping members are further dimensioned so as to form a through hole for which an inserter may be passed through.

A system and method for inserting an implant into a surgical site through a surgical corridor is also provided. The system includes an implant having a body with a pair of grooves. The pair of grooves may be on one or one both of the superior and inferior surfaces of the implant. The system further includes a guide. The implant is adaptable for use with the guide. The guide includes a pair of guide members and a clasping mechanism. Each guide member includes an elongated member. The clasping mechanism is disposed on the proximal ends of the elongated members. The clasping mechanism is configured to hold the pair of elongated members together such that the proximal ends of the guide are spaced apart from each other a predetermined distance.

The elongated members further include a pair of ribs extending axially on opposite sides. The ribs are formed on respective inner surfaces of the guide members and are configured to engage corresponding grooves on the superior and inferior surfaces of the implant.

The clasping mechanism includes a pair of clasping members configured to fit together and maintain a spatial distance between proximal ends of the respective guide members. The clasping members are further dimensioned so as to form a through hole for which an inserter may be passed through.

The method includes the step of inserting the guide members into a surgical corridor formed by a retractor. The retractor may be pulled from the surgical corridor wherein the muscle tissues are allowed to close in on the distal ends of the guide members, reducing muscle expansion around the surgical site. The implant is placed at the proximal end of the guide between the guide members so as to align the ribs of the guide member along respective grooves of the superior and inferior surfaces of the implant.

The method includes the step of passing an inserter through the through hole of the clasping member and pushing the implant down the surgical corridor towards the surgical site wherein the implant opens the surgical corridor as the implant moves towards the surgical site, thus reducing the exposure of the muscle in an expanded state and thereby reducing recovery time.

These and other features are disclosed in greater detail in the accompanying figures and the Detailed Description below.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be better understood when read in conjunction with the following drawings wherein like structure is indicated with like reference numerals and in which:

FIG. 9 is a side view of an implant being pushed through a surgical corridor defined by a pair of guide members;

FIG. 9A is a view of a retractor forming a surgical corridor;

FIG. 9C is a view showing the retractor shown in FIG. 9B removed from the surgical corridor and the implant advancing further down surgical corridor provided by the guide towards a surgical site;

FIG. 9E is a view showing the implant implanted in the surgical site;

FIG. 10a is a view from the distal end of the pair of guides looking towards the proximal end;

FIG. 10b is a view of FIG. 9 taken from the distal end of the pair of guide members;

DETAILED DESCRIPTION

An implant configured to be guided along a surgical corridor is provided. The implant includes an implant body having a superior surface and an inferior surface, a pair of side walls and a distal end opposite a proximal end. The superior and inferior surfaces may be tapered on respective distal and proximal ends of the implant body.

The implant includes a catching feature configured to help engage the implant to adjacent vertebrae. In one embodiment, the catching feature is a plurality of ridges formed on opposite superior and inferior sides of the body. The sides of the body are shown generally smooth. In one embodiment, the superior and inferior sides of the body include a pair of grooves. The grooves extend axially along adjacent sides of the superior and inferior surfaces of the implant.

The implant includes at least one biologic cavity configured to store biological bone growth material. The biological cavities may be divided by inner walls which extend between opposite sides of the implant body. Bone graft material may be inserted into the biological cavity during the course of the spinal procedure so as to help the implant retain its position between adjacent vertebrae.

As used herein, the term distal refers to the end of an implant or instrument configured to move towards a surgical site whereas the proximal end is the end opposite the distal end. As used herein, a surgical site refers to the location in which an implant is to be inserted. For illustrative purposes, here the implant is used in minimally invasive spinal surgeries. Accordingly, the surgical site is a space between adjacent vertebrae. A surgical corridor refers to an elongated opening made in the body which provides a passage within the body to the surgical site.

A guide having a pair of guide members is also provided. The guide members are configured to be assembled together about their proximal end so as to be spaced apart and form a surgical corridor. The guide members include a guide body which is a generally elongated member. The guide members have an exterior surface and an interior surface. The interior surface is in open communication with the surgical corridor. In one embodiment, the interior surface of both guide members includes a pair of ribs extending axially along opposing sides of the guide members.

A clasping mechanism is disposed on the proximal end of the guide. The clasping mechanism is configured to secure the proximal ends of the guide members together. The clasping mechanism includes a pair of clasping members. Each clasping member includes one half of a concentric bore so as to form a through hole when the clasping members are engaged. The through hole is configured for a rod of an inserter to fit within and slide through.

Figure 1:
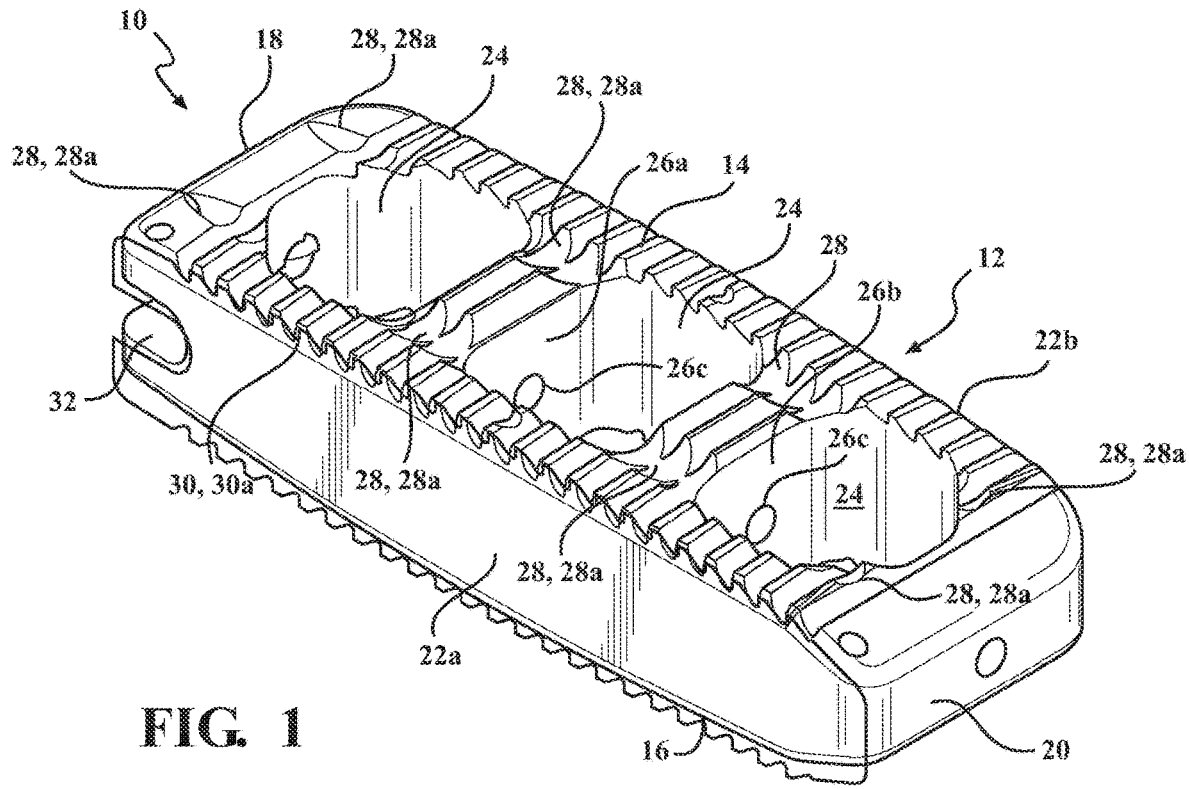
FIG. 1 is a perspective view showing the superior side of the implant.

With reference now to FIG. 1, an illustrative view of the implant 10 is provided. The implant 10 includes an implant body 12 having a superior surface 14 opposite an inferior surface 16, a proximal end 18 opposite a distal end 20, and a pair of sidewalls 22a, 22b opposite from each other. The distal and proximal ends 18, 20 of the implant body 12 may be tapered so as to facilitate the insertion of the implant 10 between adjacent vertebrae 100 (FIGS. 9C-9E). The implant 10 further includes a biological cavity 24 for holding biological material such as bone graft.

FIG. 1 provides an illustrative view of the superior surface 14 of the implant 10. However, it should be appreciated that the inferior surface 16 of the implant 10 may be identical to the superior surface 14 of the implant 10, namely the superior surface 14 of the implant 10 shows a pair of grooves 28 formed along an axis extending from a distal end 20 to a proximal end 18 of the implant body 12. The grooves 28 are formed by a plurality of generally tubular depressions 28a formed on respective superior and inferior surfaces 14, 16 of the implant body 12. Each of the generally tubular depressions 28a are axially aligned with each other so as to form a groove on each side and on each superior and inferior surface 14, 16 of the implant 10.

The grooves 28 are formed along the entire length of the implant body 12.

The implant 10 is shown as having three biological cavities 24 which bone growth material may fill. However, it should be appreciated that the implant 10 may have one or more biological cavities 24. The biological cavities 24 are defined by two inner walls 26a, 26b spaced apart from each other and extending between sidewalls 22a and 22b. The inner walls 26a, 26b may include an aperture 26c for receiving bone growth material.

Figure 4:
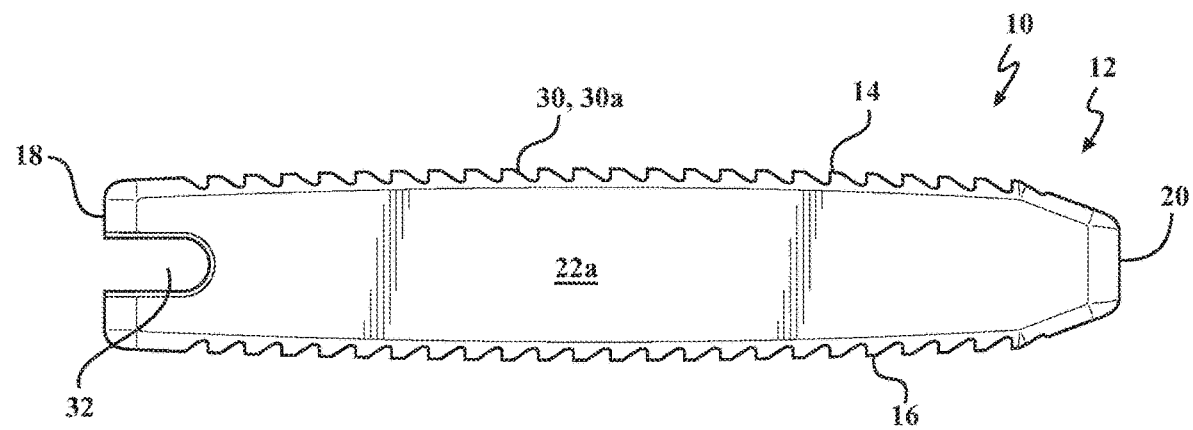
FIG. 4 is a side view of the implant shown in FIG. 1.

The implant 10 further includes a catching feature 30 configured to help engage the implant 10 to adjacent vertebra. In one embodiment, the catching feature 30 is a plurality of ridges 30a. The ridges 30a extend across the width of the implant body 12 on both the superior and inferior surfaces 14, 16. The ridges 30a are illustratively shown as having a sloped face to facilitate the introduction of the implant 10 into the surgical site 200 (FIG. 4). The ridges 30a further provide traction to help maintain the implant 10 between adjacent vertebrae 100.

The proximal end 18 of the implant 10 includes a catch 32 dimensioned to receive a head 402 of an inserter 400 (shown in FIG. 8B) so as to facilitate the push of the implant 10 along a surgical corridor 320. The catch 32 is illustratively shown as being a slot extending between the sidewalls 22a, 22b of the implant body 12 and generally equidistant between the superior and inferior surfaces 14, 16 of the implant body 12.

Figure 2:
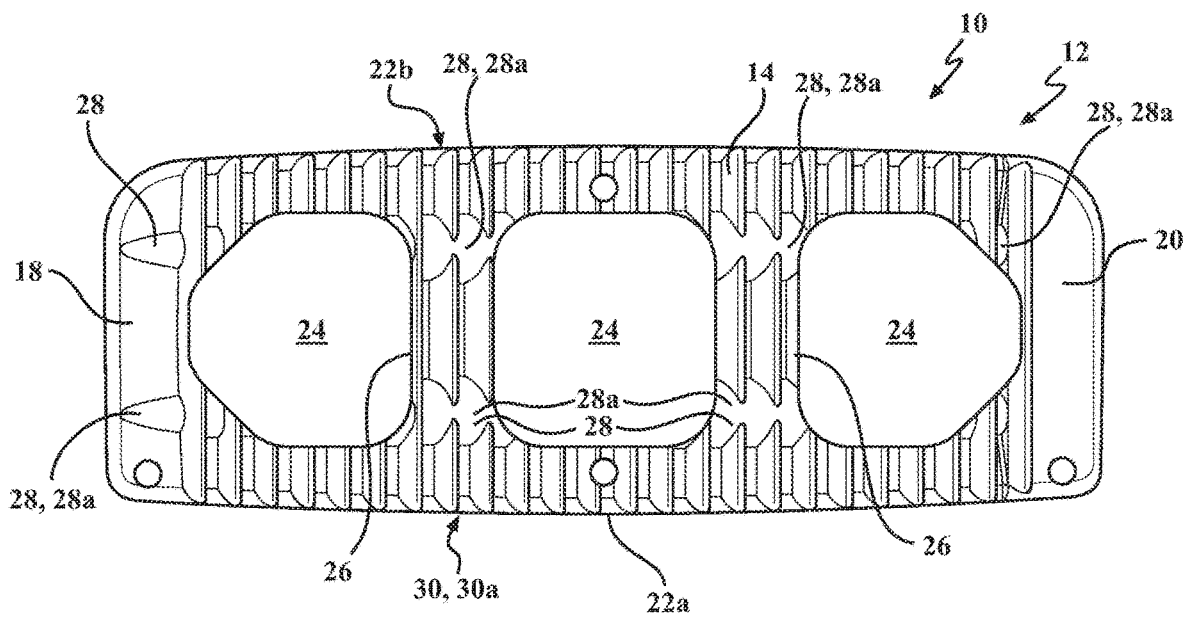
FIG. 2 is a top-down view of the implant shown in FIG. 1.
Figure 3:
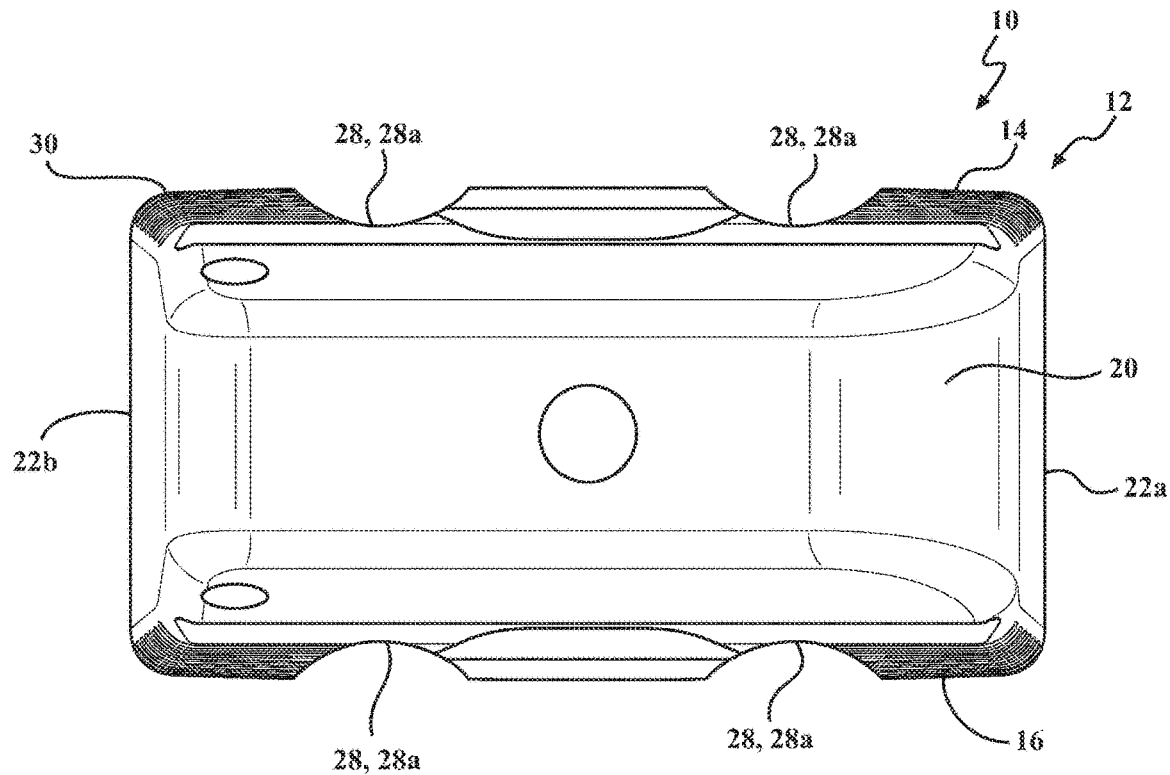
FIG. 3 is a frontal view of the implant shown in FIG. 1.

FIG. 2 shows a top-down view of the superior surface 14 shown in FIG. 1. As seen, the grooves 28 are formed along the side walls 22a, 22b of the implant 10. The grooves 28 are also formed on the inner walls 26a, 26b of the implant body 12. FIG. 3 is a frontal view of the implant 10 showing the grooves 28 formed along the superior and inferior surfaces 14, 16 of the implant body 12. FIG. 3 also shows how the grooves 28 form a C shaped cross-section having a generally uniform radius, wherein FIG. 2 shows how the circumferential surface of each of the tubular depressions 28a forming the grooves 28 change in length based upon the contours of the respective superior and inferior surfaces 14, 16 of the implant body 12.

FIG. 4 is a side view of the implant 10 showing the catch 32 disposed on the proximal end 18 of the implant 10. FIG. 4 also shows how the distal end 20 of the implant 10 is tapered, giving the implant 10 a generally bullet shape. The tapered end facilitates wedging of the implant 10 between adjacent vertebrae 100 (FIG. 9E). The ridges 30a are shown on both the superior and inferior surfaces 14, 16 of the implant 10.

Figure 5:
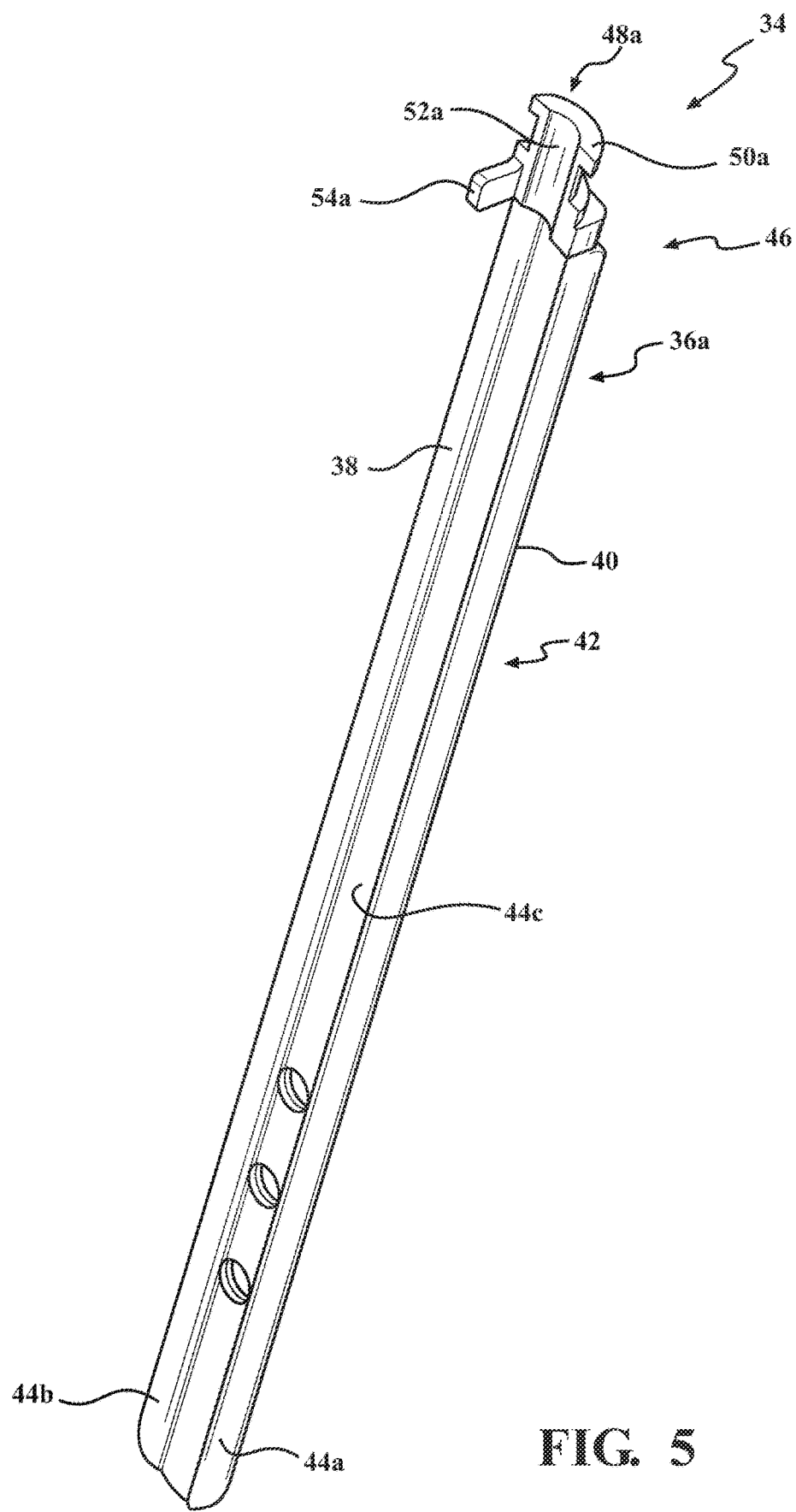
FIG. 5 is an interior view of one of the pair of guide members.
Figure 6:
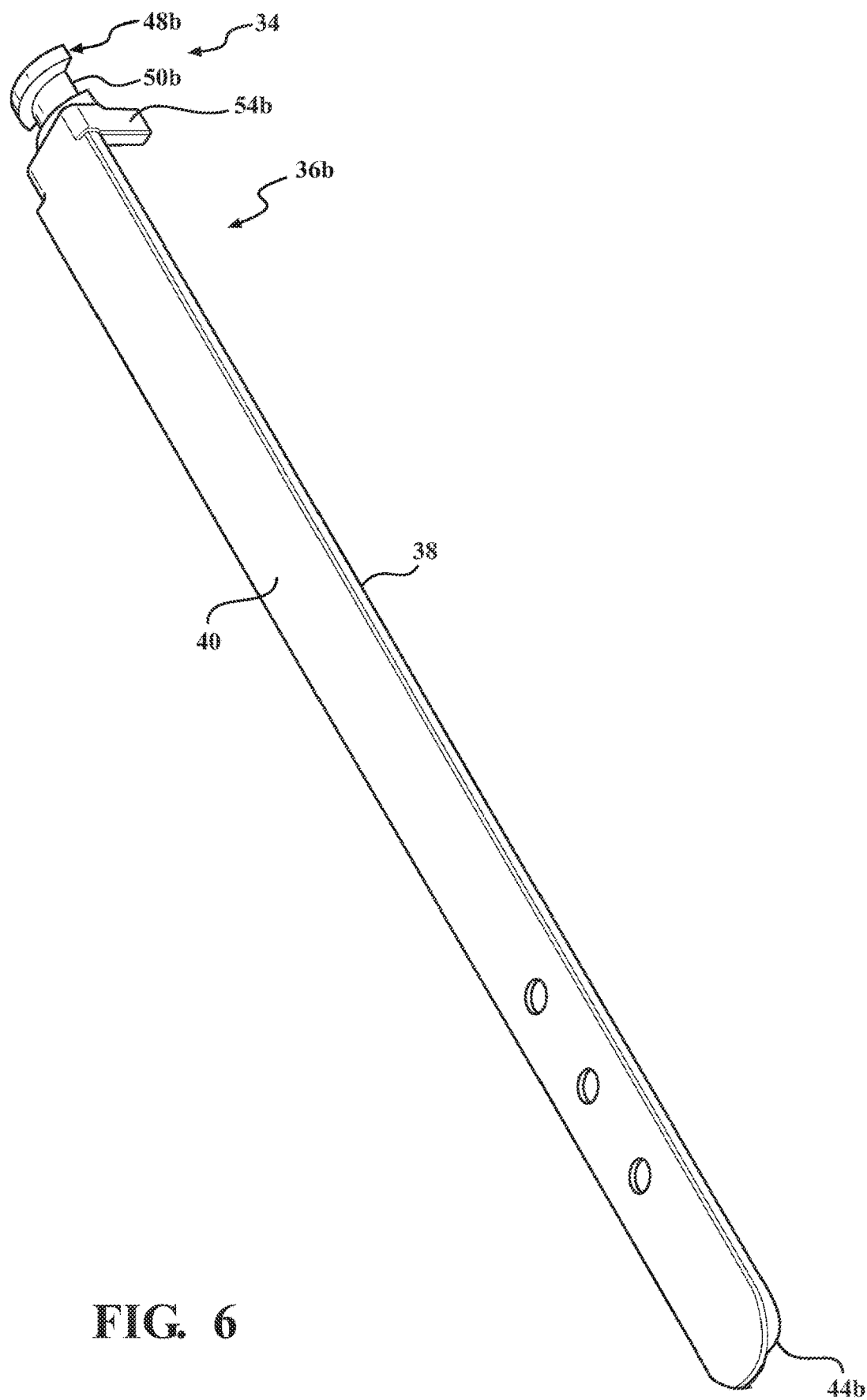
FIG. 6 is a view of the outer surface of the guide shown in FIG. 5.
Figures 7, 8:
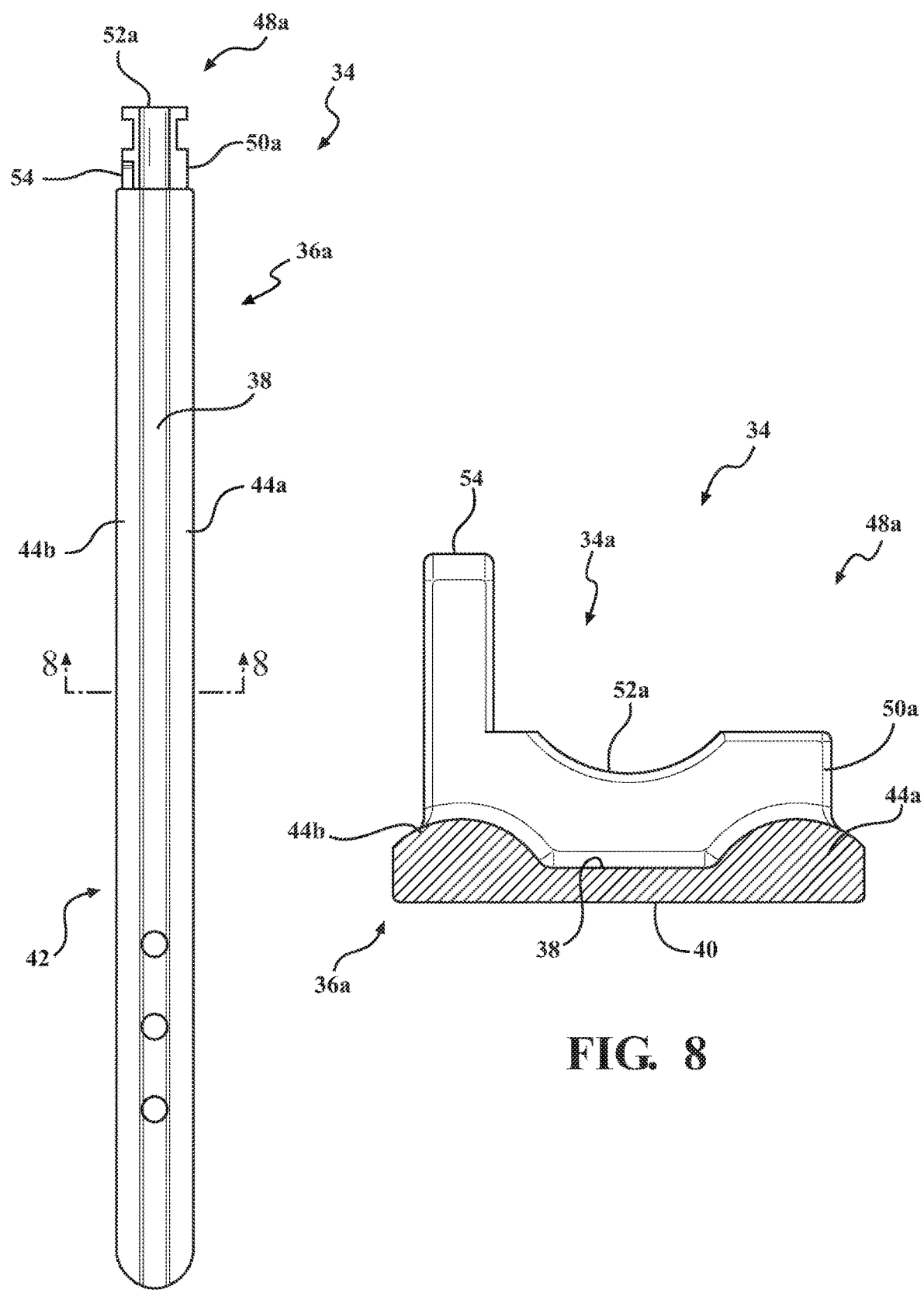
FIG. 7 is a top-down view showing the inner surface of the guide of FIG. 5.
FIG. 8 is a cross-sectional view taken along lines 8-8 of FIG. 7.

With reference now to FIGS. 5, 6, 7, 8A-8B, 9, 9A-9E, and 10, an illustrative embodiment of a guide 34 is provided. The guide 34 includes a pair of guide members 36a, 36b. Each of the guide members 36a, 36b is a generally elongated member. FIG. 5 shows one of the pair of guide members 36a and FIG. 6 shows the other of the pair of guide members 36b. The guide members 36a, 36b may be formed of a resilient and durable material such as titanium. The guide members 36a, 36b have an inner surface 38 opposite an outer surface 40. The inner surface 38 forms the surgical corridor 320 (FIG. 8B).

A view of the inner surface 38 is shown in FIG. 5, and the outer surface 40 is shown in FIG. 6. The guide members 36a, 36b include an elongated body 42 having a pair of ribs 44a, 44b disposed along opposite sides of the elongated body 42 so as to form an elongated groove 44c. The ribs 44a, 44b extend the axial length of the elongated body 42.

The guide 34 further includes a clasping mechanism 46 disposed on the proximal end of the guide 34. The clasping mechanism 46 is configured to couple the proximal ends of the guide members 36a, 36b together and also provide a bore through which an inserter may pass. In one embodiment of a clasping mechanism 46, the clasping mechanism 46 includes a pair of clasping members 48a, 48b coupled together or engaged so as to form a generally cylindrical body 50 having a through hole 52 (FIGS. 9C and 10a). The clasping mechanism 46 is configured to hold the proximal ends of the guide 34 together, and to accommodate the passage of the inserter 400 (e.g., shown in FIGS. 8B and 9C). Accordingly, the distal ends of the guide 34 are not supported. In particular, the distal ends of the guide members 36a, 36b are free to move relative to each other. The distal ends of the guide members 36a, 36b may be sharpened to help the guide 34 find purchase in between adjacent vertebrae 100.

FIG. 5 is a view taken of the inner surface 38 of one of the pair of guide members 36 showing one of the pair of clasping members 48a. The clasping member 48a includes a first cylindrical body portion 50a defining generally one half of the cylindrical body 50 and a first through hole portion 52a forming one half of the through hole 52. It should be appreciated that clasping member 48b is configured to engage clasping member 48a so as to form the generally cylindrical body 50 having the through hole 52, and thus clasping member 48b includes a second cylindrical body portion 50b forming the other half of the cylindrical body 50 and a second through hole portion 52b forming the other half of through hole 52. That is, first cylindrical body portion 50a forms one half of a concentric bore and the second cylindrical body portion 50b forms another half of a concentric bore, the two halves of the concentric bore forming the through hole 52.

The clasping members 48a, 48b further includes a spacer 54a, 54b, respectively, extending from an inner concave portion of the respective first and second cylindrical body portion 50a, 50b. The spacer 54b is located on an opposite side of the through hole 52 (FIG. 10a) from the spacer 54a shown in FIG. 5. Thus, engagement of the clasping members 48a, 48b when placed together space the elongated body 42 of respective guide members 36a, 36b apart from each other to form the surgical corridor 320. The spacers 54a, 54b are configured to abut against opposing surfaces of respective second and first cylindrical body portions 50b, 50a so as to maintain the proximal end of the guide members 36a, 36b apart from each other and yet allow the distal ends of the guide members 36a, 36b to close in on each other.

With reference to FIG. 10a, a view of the pair of guide members 36a, 36b assembled together and viewed from the distal end of the guide 34 is provided. FIG. 10a shows the pair of guide members 36a, 36b wherein the clasping members 48a, 48b are fitted together and the surgical corridor 320 is formed. As seen, the four ribs 44a, 44b are shown. One pair of ribs 44a, 44b are disposed on the first guide member 36a and one pair of ribs 44a, 44b are disposed on the second guide member 36b. FIG. 10a also provides a view of the through hole 52.

FIG. 10b is a view of FIG. 9 taken from the distal end of the pair of guide members 36a, 36b. FIG. 10b shows each rib 44a, 44b engaging respective grooves 28, 28a. Each rib 44a, 44b is dimensioned so as to be longer than the depth of the respective grooves 28, 28a. In one embodiment, the ribs have a convex outer surface so as to have a radius R which is longer than the depth of the respective groove 28, 28a so as to position the outer surface 14, 16 of the implant 10, in particular the superior surface 14 and inferior surface 16, apart from the inner surface 38 of the elongated body 42 of respective guide members 36a, 36b. Thus, movement of the implant 10 along the surgical corridor 320 is conducted by the sliding engagement of the ribs 44a, 44b with respect to the grooves 28, 28a. In other words, the superior 14 and inferior surfaces 14, 16 do not slide against the inner surface 38 of the respective guide members 36a, 36b as the implant 10 is pushed down the surgical corridor 320.

For illustrative purposes, the ribs 44a, 44b are shown on the outer sides of each guide member 36a, 36b, and the implant 10 is wider than the guide members 36a, 36b. However, it should be appreciated that the implant 10 may be dimensioned so as to be narrower than the guide members 36a, 36b.

Figure 11:
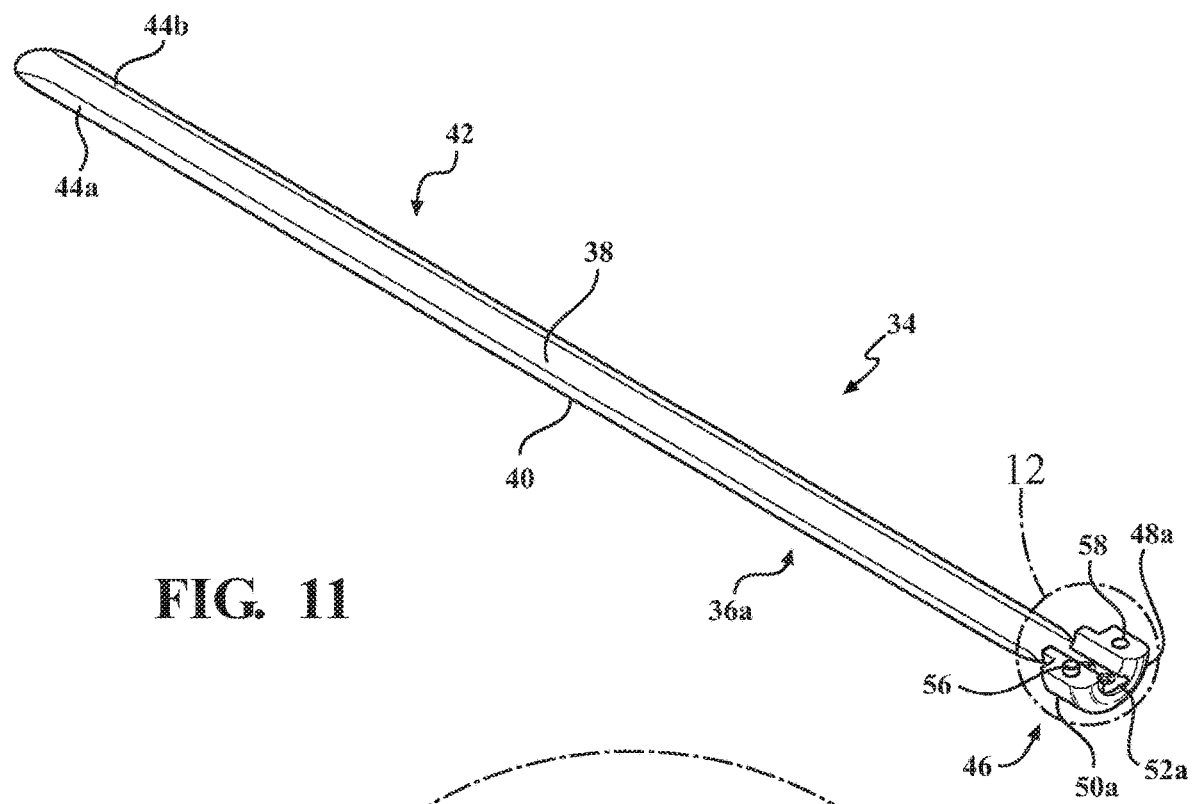
FIG. 11 is an alternative embodiment of a clasping mechanism.
Figure 12:
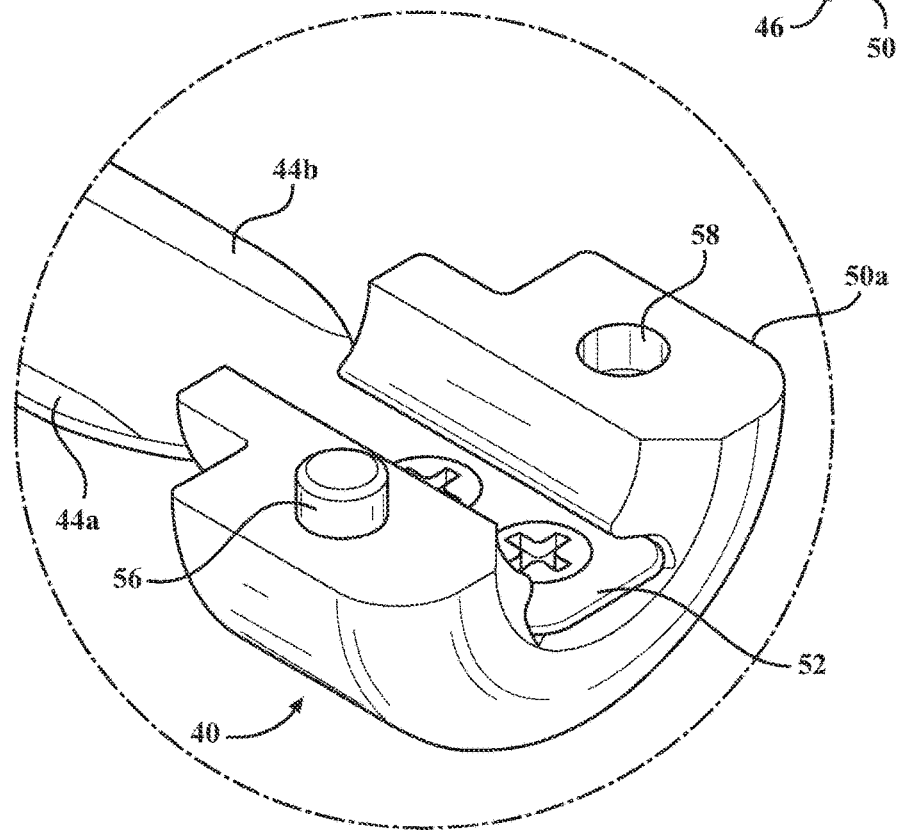
FIG. 12 is an isolated view of the clasping mechanism shown in FIG. 11.

FIGS. 11 and 12 provide an alternative embodiment of the clasping members 48a, 48b. Mating or inner surfaces of the first and second cylindrical body portions 50a, 50b (only first cylindrical body portions 50a shown) include a peg 56 and an opening 58. The peg 56 may be magnetic and the cylindrical body may be formed of a material configured to emit a magnetic field. Accordingly the peg 56 may be magnetically engaged to a corresponding opening 58. It should be appreciated that only one half of the clasping mechanism 46 is shown, that is clasping member 48a, but that clasping member 48b is symmetrical to clasping member 48a and thus an explanation of clasping member 48a is sufficient to describe clasping member 48b.

Figure 9B:
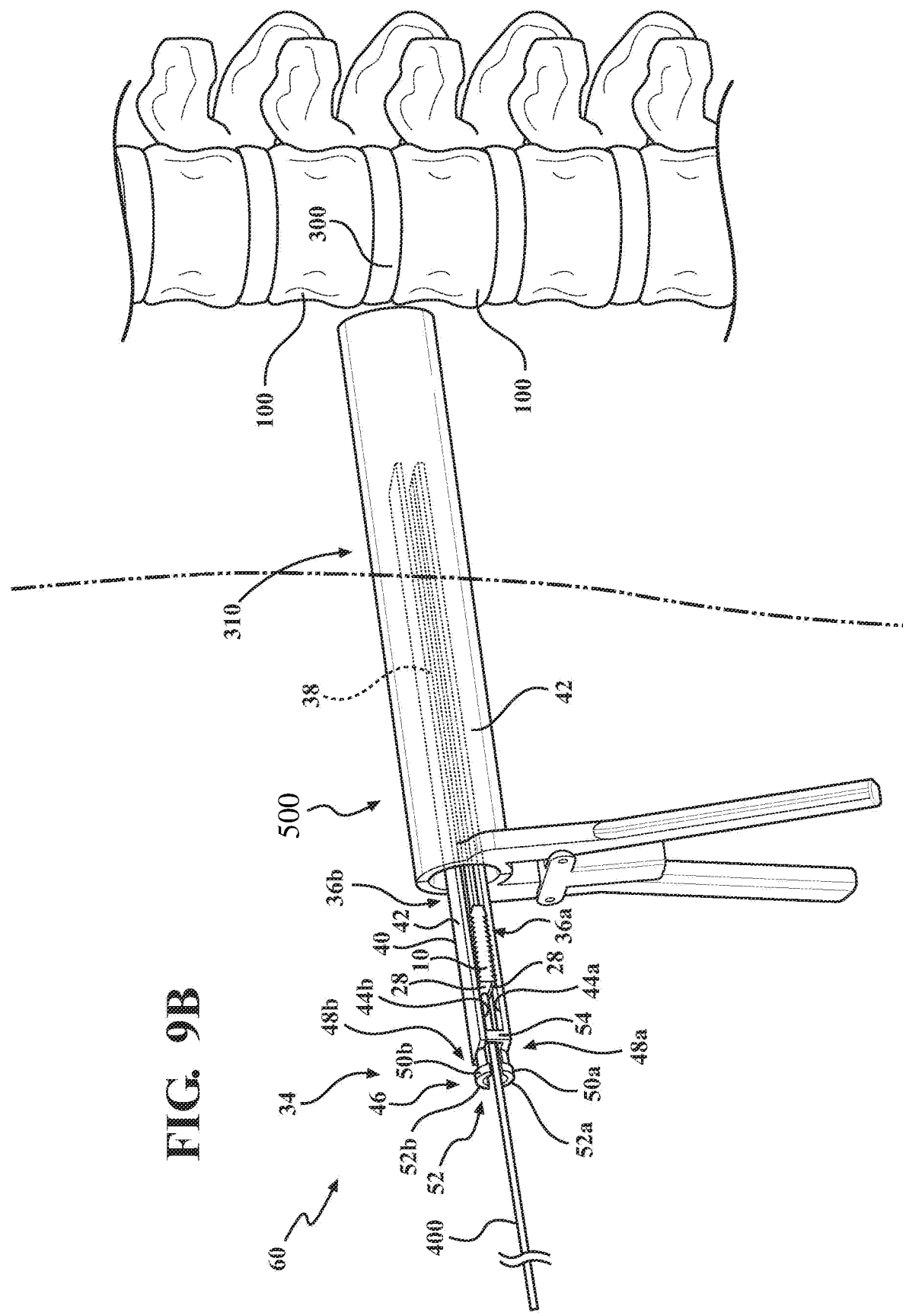
FIG. 9B is a view showing a guide with a pair of guide members inserted between retractor blades into the surgical corridor formed by the retractor and an implant between the pair of guide members.
Figure 9D:
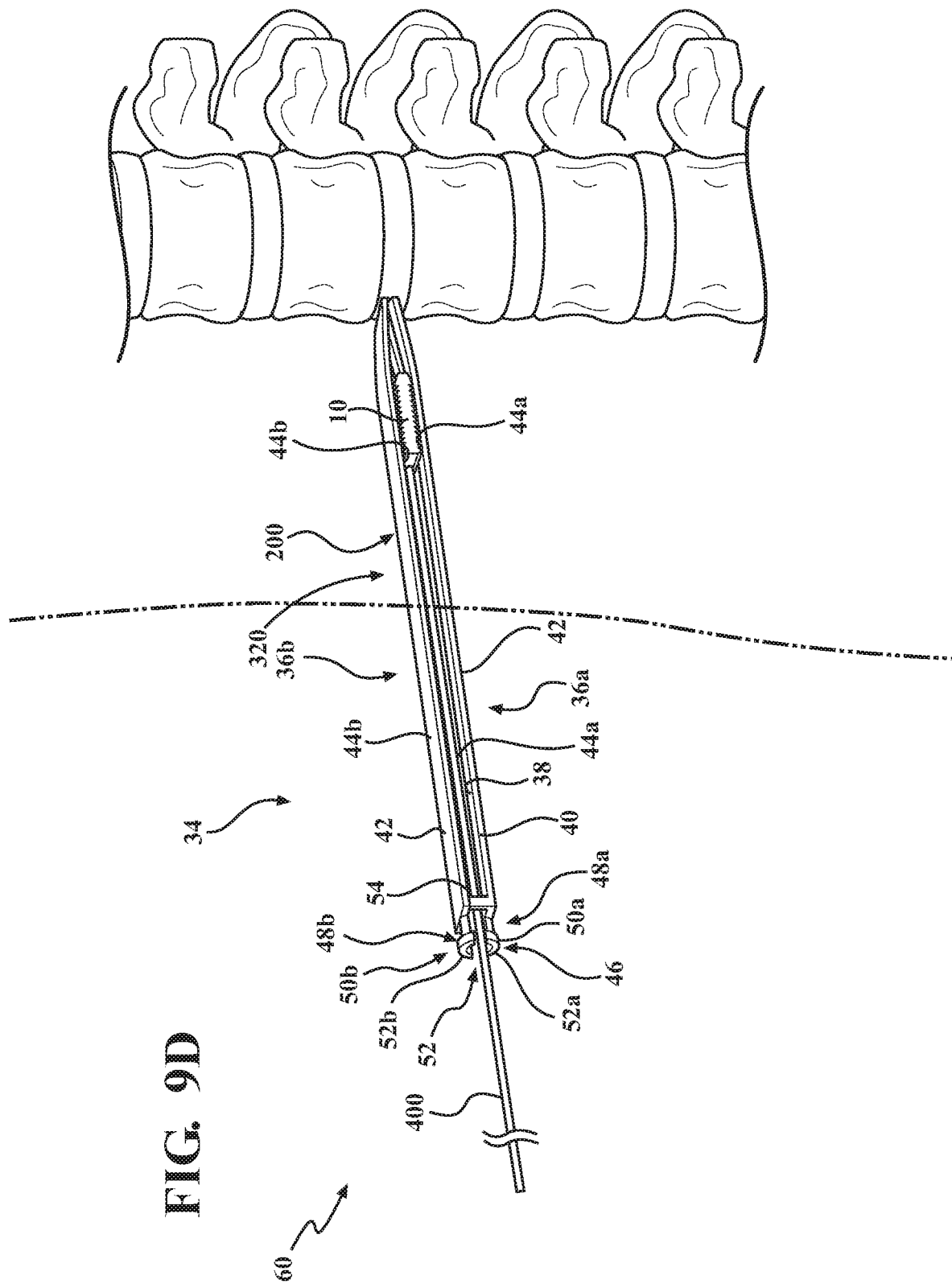
FIG. 9D is a view showing the implant advancing further down the surgical corridor towards the surgical site relative to FIG. 9C.

With reference now to FIGS. 9A-9E, a system 60 for performing a minimally invasive spinal procedure wherein an implant 10 is introduced into a surgical site 300 is provided. The system 60 includes an instrument 500 configured to create a surgical corridor 310, as shown in FIG. 9A. Such instruments 500 are currently known and used and illustratively include a retractor, which may also be referenced herein as retractor 500.

The system 60 further includes an implant 10 illustratively shown in FIGS. 9B-9E and also FIGS. 1-4. The implant 10 includes an implant body 12 having a superior surface 14 and an inferior surface 16. A pair of grooves 28 are disposed on both the superior and inferior surfaces 14, 16. The grooves 28 are opposite each other and extend the length of the implant body 12. The distal end of the implant 10 may be tapered so as to facilitate the insertion of the implant 10 between adjacent vertebrae 100 at the surgical site 300.

The system further includes a guide 34 having a pair of guide members 36a, 36b. The guide members 36a, 36b have an elongated body 42. The inner surface 38 of the elongated body 42 defines the surgical corridor 310. A pair of ribs 44a, 44b extend axially on opposite sides of the inner surface 38 of the elongated bodies 42. The ribs 44a, 44b are configured to slidingly engage respective grooves 28 of the implant 10.

With reference now to FIG. 9B, the guide 34 with the implant 10 is inserted into the surgical corridor 310 formed by the instrument 500. The implant 10 is placed between the guide members 36a, 36b wherein the ribs 44a, 44b are aligned to engage respective grooves 28. The instrument 500 may then be removed from the body, wherein the muscles are free to close the distal end of the guide members 36a, 36b towards each other with a surgical corridor 320 provided by the guide 34 with guide members 36a, 36b.

The system 60 may further include an inserter 400 wherein the inserter 400 is configured to push the implant 10 down the surgical corridor 320 between guide members 36a, 36b to the surgical site 300, as shown in FIGS. 9B-9E. FIG. 9B shows the inserter 400 engaged with the implant 10 and the implant 10 disposed between guide members 36a, 36b. The grooves 28 of the implant 10 are received by the ribs 44a, 44b of the respective guide members 36 so as to control the axial movement of the implant 10 down the surgical corridor 320 to the surgical site 300.

FIGS. 9C-9E show the instrument 500 removed from the surgical site, thus reducing the size of the surgical corridor 310 (shown in FIGS. 9A and 9B) down to the size of the surgical corridor 320. In particular, the retractor 500, shown in FIGS. 9A and 9B, maintains a generally cylindrical shaped surgical corridor 310 as the retractor blades are formed by a durable and rigid material such as titanium and the ends of the blades are pressed against each other. Accordingly, with the retractor 500 removed, the muscles close in on the guide 34. In particular, musculature load compresses the guide members 36a, 36b together minimizing the size of the surgical corridor 320. Further, as the implant 10 is pushed towards the surgical site 300, the guide members 36a, 36b overcome the musculature load, opening the surgical corridor 320 as the implant 10 moves towards the surgical site 300, as shown in FIGS. 9C-9E.

Figure 13:
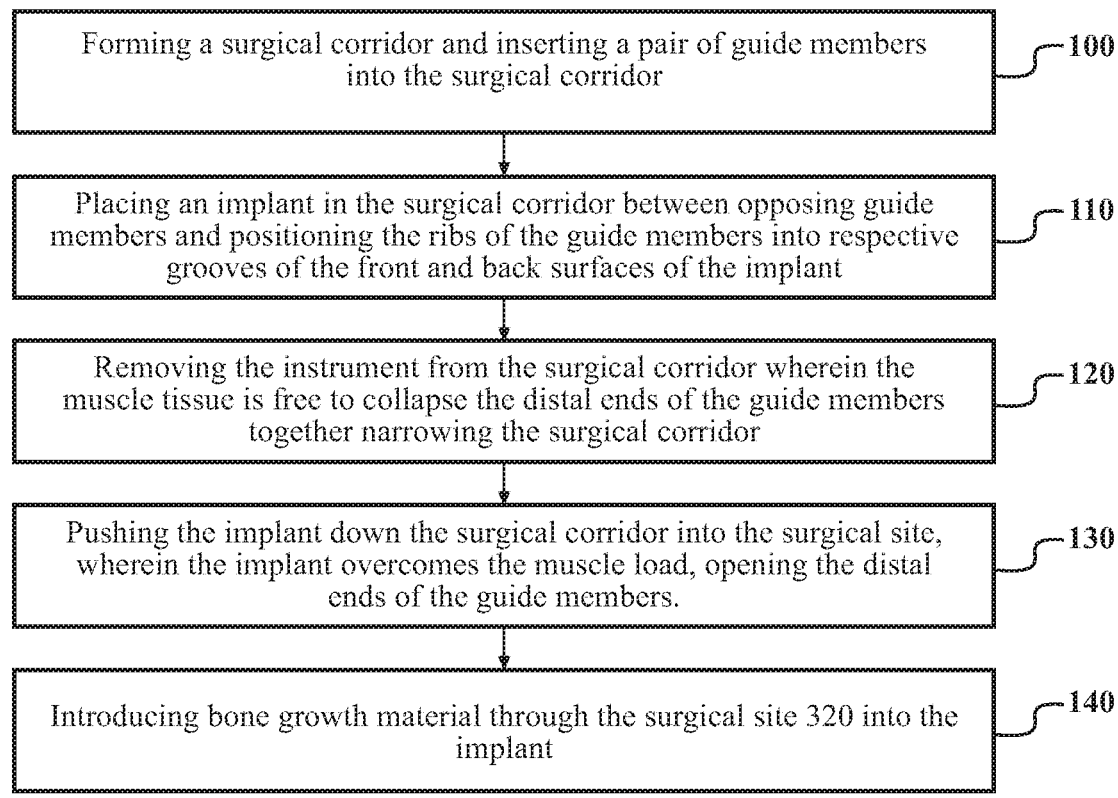
FIG. 13 is a diagram showing a method of inserting an implant into a surgical site.

With reference now to FIG. 13, a method 62 of inserting an implant 10 into a surgical site 300 is also provided. The surgical site 300 is disposed between two vertebrae 100. The surgical corridor 310 is formed by an instrument 500 such as a retractor 500. The method 62 includes an implant 10. The implant 10 includes an implant body 12 having a superior surface 14 and an inferior surface 16. A pair of grooves 28 are disposed on both the superior and inferior surfaces 14, 16. The grooves 28 are opposite each other and extend the length of the implant body 12. The distal end of the implant 10 may be tapered so as to facilitate the insertion of the implant 10 between adjacent vertebrae 100 at the surgical site 300.

The method 62 further includes a guide 34 having a pair of guide members 36a, 36b. The guide members 36a, 36b have an elongated body 42. The inner surface 38 of the elongated body 42 defines the surgical corridor 320. A pair of ribs 44a, 44b extend axially on opposite sides of the inner surface 38 of the elongated bodies 42. The ribs 44a, 44b are configured to slidingly engage respective grooves 28 of the implant 10.

The method begins with step 100 of forming the surgical corridor 310 using the instrument 500. It should be appreciated that other instruments such as a dilator may be used to create an initial opening which is gradually expanded until the retractor 500 is inserted into the surgical corridor 310. The method proceeds by inserting the pair of guide members 36a, 36b into the surgical corridor 310 wherein the clasping members of the guide members 36 hold the proximal ends of the guide members 36a, 36b together so as to space the distal ends of the guide members 36a, 36b apart forming a generally uniform surgical corridor 310 uniform in dimension along the axis of the corridor.

The method 62 proceeds to step 110 of placing an implant 10 in the surgical corridor 310 between opposing guide members 36a, 36b and positioning the ribs 44a, 44b of the guide members 36 into respective grooves 28 of the superior and inferior surfaces 14, 16 of the implant 10. It should be appreciated that the guide 34 may be placed within the surgical corridor 310 formed by the retractor 500 with the implant 10 between guide members 36a, 36b or the implant 10 is inserted between guide members 36a, 36b after the guide 34 is inserted into the surgical corridor 310. The method 62 proceeds to step 120 of removing the instrument 500 (retractor) from the surgical corridor 310 wherein the muscle tissue is free to collapse the distal ends of the guide members 36a, 36b together narrowing the surgical corridor 310 formed by the retractor 500. That is, removal of the instrument 500 collapses the surgical corridor 310 down to surgical corridor 320 provided by the guide members 36a, 36b.

The method proceeds to step 130 of pushing the implant 10 down the surgical corridor 320. The implant 10 may be pushed down the surgical corridor 320 with an inserter rod 400 wherein the inserter rod 400 is positioned through the through hole 52 formed by the clasping mechanism 46 wherein the pressure from the muscle tissue narrows the surgical corridor 310 formed by the guide members 36a, 36b as the implant 10 is pushed past the guide members 36a, 36b as shown in FIG. 9E. The implant 10 is introduced into the surgical site 300 as shown in FIG. 9E. The method may further include step 140 of introducing bone growth material into the implant 10. Accordingly, the method removes the retractor 500 and utilizes a guide 34 to insert the implant 10 thus preventing the muscles from being in an expanded state longer relative to the use of retractors and thus minimizing recovery time for the patient.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. For instance, the implant may have one groove extending axially along adjacent sides if the superior and inferior surface of implant and not a pair of grooves. In such an embodiment, the guide may have guide members each having only one rib so as to guide the implant towards the surgical site along respective grooves. Alternatively, the implant may have only one groove, and the guide may have a pair of guide members, for which only one guide member has a rib working in concert with the groove so as to guide the implant towards the surgical site. It should also be noted that the instrument, system and method described herein is illustrated in an anterior approach, but that the instrument, system and method described herein may be used in other surgical procedures to include a lateral or posterior approach.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. In one embodiment, the terms "about" and "approximately" refer to numerical parameters within 10% of the indicated range.

The terms "a," "an," "the," and similar referents used in the context of describing the embodiments of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the embodiments of the present disclosure and does not pose a limitation on the scope of the present disclosure. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventor for carrying out the embodiments of the present disclosure. Of course, variations on these described embodiments will become apparent to those of ordinary skill in the art upon reading the foregoing description. The inventor expects skilled artisans to employ such variations as appropriate, and the inventor intends for the embodiments of the present disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of this disclosure so claimed are inherently or expressly described and enabled herein.

Furthermore, if any references have been made to patents and printed publications throughout this disclosure, each of these references and printed publications are individually incorporated herein by reference in their entirety.

In closing, it is to be understood that the embodiments disclosed herein are illustrative of the principles of the present disclosure. Other modifications that may be employed are within the scope of this disclosure. Thus, by way of example, but not of limitation, alternative configurations of the embodiments of the present disclosure may be utilized in accordance with the teachings herein. Accordingly, the present disclosure is not limited to that precisely as shown and described.

The invention claimed is:

1. A method of inserting an implant into a surgical site through a surgical corridor formed by an instrument, the method comprising the steps of:

inserting a guide into the surgical corridor formed by the instrument, the guide having a pair of guide members, each of the pair of guide members have an elongated body, the elongated body having an inner surface defining the surgical corridor, a proximal end of each of the guide members coupled together and together forming a through hole, wherein a distal end of each of the guide members are free to move relative to each other;

placing an implant in the surgical corridor between opposing guide members the implant having a superior surface and an inferior surface that each engage a respective guide member;

at least partially removing the instrument from the surgical corridor to allow muscle tissue to collapse the distal ends of the guide members narrowing the surgical corridor; and advancing the implant through the surgical corridor and into the surgical site.

2. The method of claim 1, wherein each of the pair of guide members further includes at least one rib, the at least one rib extending axially along a respective elongated body.

3. The method of claim 2, wherein the implant includes grooves extending axially along adjacent sides of superior and inferior surfaces of the implant and further comprising positioning the at least one rib of each guide member into a respective groove of the superior and inferior surfaces of the implant, and wherein the at least one rib is configured to slidingly engage the respective groove of the implant.

4. The method of claim 3, further including the step of inserting an inserter through the through hole and pushing the implant down the surgical corridor and between the pair of guide members.

5. The method of claim 4, further including the step of introducing bone growth material into the implant.

6. The method of claim 2, wherein the implant includes a groove extending axially along adjacent sides of superior and inferior surfaces of the implant and further comprising positioning the at least one rib of each guide member into a respective groove of the superior and inferior surfaces of the implant, and wherein the at least one rib of each guide member are configured to slidingly engage the respective grooves of the implant.

7. The method of claim 1, wherein each of the pair of guide members further includes two ribs, the two rib extending axially along the elongated body of each guide member.

8. The method of claim 7, wherein the implant includes two grooves on both superior and inferior surfaces of the implant and further comprising positioning the two ribs of each guide member into a respective groove of the superior and inferior surfaces of the implant, and wherein the two are configured to slidingly engage the grooves of the implant.

9. The method of claim 8, further including the step of inserting an inserter through the through hole to advance the implant down the surgical corridor and between the pair of guide members.

10. The method of claim 9, further including the step of introducing bone growth material into the implant.

11. The method of claim 1, wherein the proximal end of each guide member has a clasping member with a spacer configured to engage a corresponding clasping member on the other guide member.

12. The method of claim 11, wherein the spacer of each guide member creates a space between the proximal ends of each guide member.

13. The method of claim 12, wherein the space between the proximal ends of the guide members forms a part of the through hole.

* * * * *